US00PP13253P3

(12) United States Plant Patent
Cosner

(10) Patent No.: US PP13,253 P3
(45) Date of Patent: Nov. 19, 2002

(54) *LOBELIA ERINUS* PLANT NAMED 'TILU'

(75) Inventor: Harlan B. Cosner, Broadbent, OR (US)

(73) Assignees: Harlan Cosner, Rogue River, OR (US); Sue Cosner, Rogue River, OR (US)

( * ) Notice: Subject to any disclaimer, the term of this patent is extended or adjusted under 35 U.S.C. 154(b) by 0 days.

(21) Appl. No.: 09/826,492

(22) Filed: Apr. 4, 2001

(65) Prior Publication Data

US 2002/0148022 P1 Oct. 10, 2002

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Susan B. McCormick
(74) *Attorney, Agent, or Firm*—Ganz Law, PC; Bradley M. Ganz, Esq.

(57) ABSTRACT

A new and distinct cultivar of 'Lobelia erinus' having pendulous stems, freely branching plant habit, light blue flowers with a white eye that are produced continuously throughout the growing season, dark green to bronzish green foliage, and good heat tolerance.

1 Drawing Sheet

BACKGROUND OF THE INVENTION

Field of Invention

Figure 1:
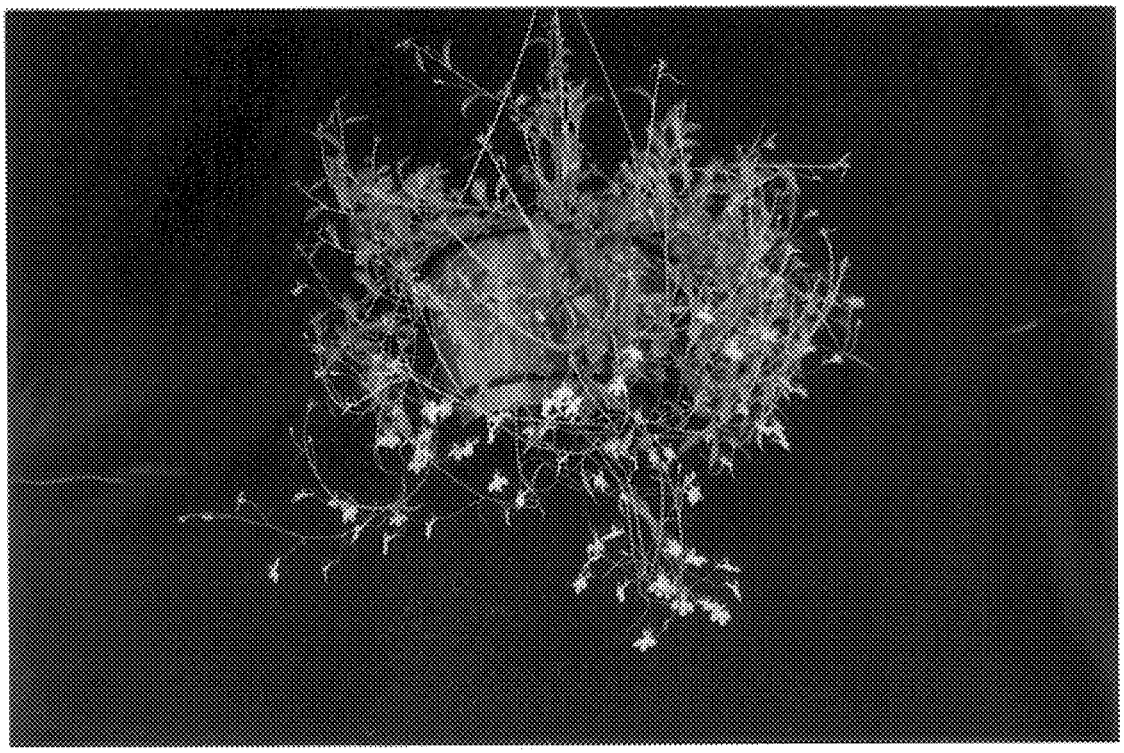
Figure 2:
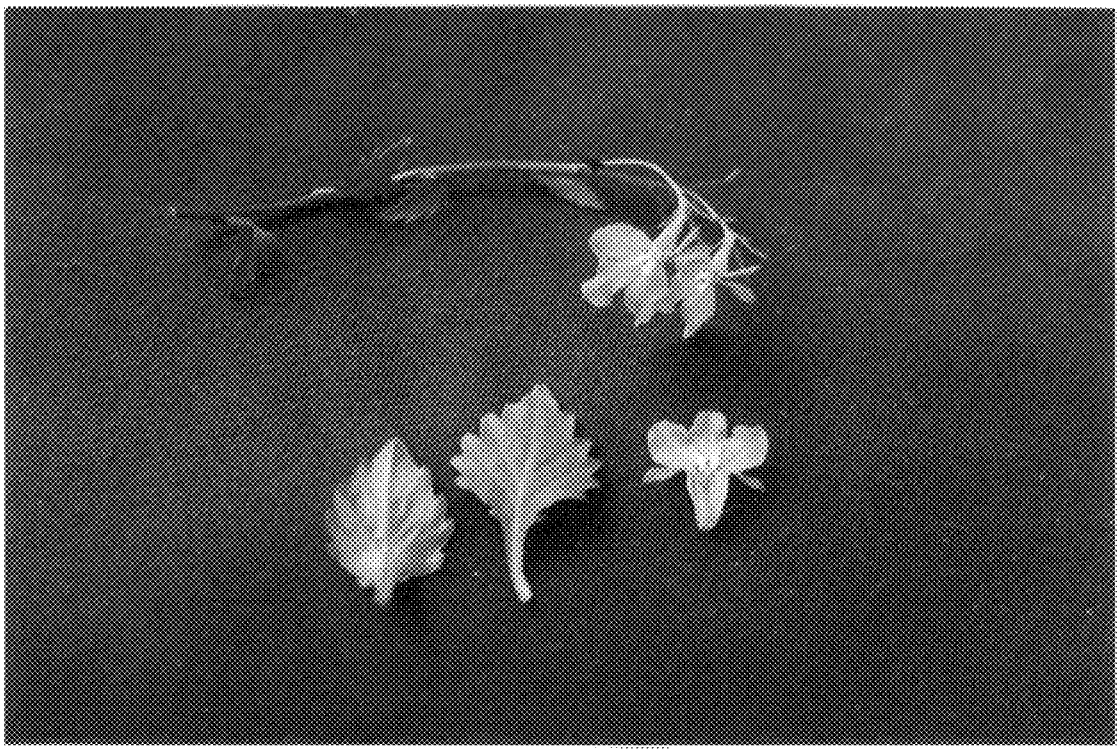

The present invention relates to a new and distinct cultivar botanically known as 'Lobelia erinus', and hereinafter referred to by the cultivar name 'TiLu'.

The cultivar of the accompanying photograph was developed and selected in a controlled breeding program in Coquille, Oreg. by the Inventor, Harlan Cosner, as described herein.

The plant is intended primarily to be ornamentally used in, for example, hanging baskets, patio tubs, window boxes, as bedding plants and other such application.

DESCRIPTION OF THE RELEVANT ART

The seed parent of the present invention was 'Sapphire Lobelia' (not patented), and the pollen parent was 'Crystal Palace Lobelia' (not patented), both of which are commercially available as seed-produced varieties though most seed catalogs. The inventor to date has been unable to reproduce the instant cultivar from seeds.

The seed parent is pendulous, growing much more airy and open with less branching than the present invention. The flower color of the seed parent is a very dark blue with a white eye, and the foliage is medium green on the upper surface and a lighter green on the lower surface. When grown under direct sunlight without cover and/or at temperatures below those in the specification, flower color intensified to a darker blue. The pollen parent is a short upright variety with stem growth generally less than 15 cm. The flower color is also a very dark blue.

The cultivar of the present invention has light blue flowers, which sets it apart from either parent, both of which have dark blue flowers. The foliage of the present invention is dark green on the top surface, and dark bronzy-green on the underside surface compared to the seed parent, which has a medium green foliage on the top surface and a lighter green foliage on the underside surface. The present invention is also pendulous in comparison to the pollen parent, which is very short with an upright habit. The present invention is more freely branching than the seed parent, and the stems of the present invention are more compact than the seed parent.

The plant was discovered as a result of a planned breeding program. The inventor made the cross at Coquille, Oreg., and the first asexual propagation was completed at Coquille, Oreg., on Jul. 15, 1997. Successive generations of asexual reproductions have proven the plant to be stable.

Color references are according to The Royal Horticultural Society Colour Chart, except where general terms of ordinary dictionary significance are used.

SUMMARY OF THE INVENTION

A new and distinct cultivar of *Lobelia erinus* having pendulous stems, freely branching plant habit, light blue flowers with a white eye that are produced continuously throughtout the growing season (generally frost-free period spring through fall), dark green to bronzish green foliage, and good heat tolerance.

DESCRIPTION OF THE PHOTOGRAPHS

The attached color photographs illustrate the cultivar of the present invention.

PLANT DESCRIPTION

The following observations, measurements and description of the plant and flowers are based on the following environment and cultural practices at Broadbent, Oreg. The description below is of the plant shown in the photographs. The following measurements, values and comparisons describe plants grown under a double layer of polyethylene film, with temperatures ranging from about 50° F. to about 75° F. during the daytime. Night minimum temperatures were maintained at about 50° F. The individual plants were grown in 10-inch hanging baskets in a soiless medium consisting of a Peatlite-type mix. Plants were liquid fed with 20-10-20 plus minor elements. The plant grows to stem length of about 35 cm. in about 12 weeks from a rooted cutting. The cutting types were lateral stems with leaves. Cuttings were stuck in about the first week of September 2000; flowering began in about the first week of Februrary 2001. Light levels were 1,000–6,000 ft. candles, depending on cloud cover.

The plant of the present invention has not been observed in all possible environmental and/or cultural conditions. The phenotype may vary significantly with variations in environment such as temperature, light level, humidity and also with cultural practices such as fertility, soil and water quality.

The accompanying photographs illustrate the overall appearance and the flower color of the cultivar of the present invention described herein. The photographs were taken of a mature plant at about 12 weeks of age from rooted cutting during early inflorescence. Finishing times could vary with the time of year cuttings are stuck, e.g., sticking in spring would lead to quicker finishing times than in fall or winter.

There may be variations between the colors in the photographs and the colors in the following description due to, for example, light reflectance, the amount of blue or red light captured in the film, and/or propagation stress. If such variations occur, then written description shall control.

The following description was taken of the TiLu cultivar shown in the photographs.

Parentage: The new cultivar was developed by standard cross-pollination. As noted above, its seed parent was a 'Sapphire Lobelia' (not patented), and the pollen parent was a 'Crystal Palace' (not patented) Lobelia.

Propagation:

*Type of cutting.*—Lateral stems with leaves.

*Time to initiate roots.*—Approximately 14 to 21 days.

Appearance and form of mature plant:

*Plant form and habit.*—Plant for is free branching and pendulous.

*Plant size.*—Mature plants are about 10 cm. in height, and about 50 cm. in width. Both of these measurements are a function of age, the above environmental and cultural practices, and can vary accordingly.

*Rooting habit.*—Roots are fibrous, freely branching, and often stems are callused above ground at the nodes, with the roots easily forming from these callused nodes. The application of rooting hormones is not needed on any cuttings, even those without callus present at the time of sticking.

*Stems.*—Pendulous, with length at first flower production of about 40 cm. Color does not match any in the chart and is closest to, but darker than, 199A with a greenish overtone. Diameter of stems is about 2 mm., and internode length is about 2 cm.

*Foliage.*—Leaves are alternate and flat, generally curved at the petiole to grow horizontal when stems are growing vertical from a hanging basket. Shape is ovate to nearly orbical with lobed margins, acute apex, and attenuate base. There is no real definition between petiole and leaf other than the margin becomes entire along the petiole.

*Foliage size.*—The size of the largest leaves is about 3.5 cm long and about 2.5 cm. wide.

*Foliage color.*—Adaxial surface color is 147A, with lateral venation being distinguishable to indistinguishable from the color of the remainder of the leaf surface. The main vein is close to 146A. The abaxial surface is close to 200C with lateral veins ridged from the surface, appearing close to 200B, and a center vein appearing close to 146A.

*Foliage texture.*—The foliage texture is satiny and smooth.

*Petioles.*—Petioles are about 1 cm. long and flat on the upper surface with the color being close to 147A. The abaxial surface is flat with the exception of a center vein which is prominent. The color does not match any in the cart, but appears close to 200D with overtones appearing close to 146D. The main vein appears to be close to 146A.

*Flower habit.*—Flowers are produced freely and continuously throughout the growing season.

*Flower size.*—Flowers are about 2.1 cm. wide and 2 cm. high. The top three lobes of each petal are about 0.7 cm. wide and 1.2 cm. deep. They are elliptic in shape with obtuse apex and entire margin and cuneate base. Each of the two side lobes is about 2 mm. wide and about 0.7 cm. in length. They are oblanceolate in shape with acute apex and entire martin and cuneate base. The above measurements refer to the larger flowers.

*Flower texture.*—Smooth and satiny.

*Flower count.*—Usually at least 10 flowers per spike with normally several hundred open per plant.

*Natural flowering season.*—The frost-free period from spring through fall in most growing areas of the United States. First inflorescence appeared about 12 weeks from transplant of a rooted cutting in early fall.

*Duration of flowers.*—A single flower would typically last about four days, depending on environmental conditions.

*Flowers borne.*—Flowers are produced one per peduncle on spikes which from at the apex of the stems.

*Flower shape and color.*—There is one petal with five lobes, with a base section which is rolled into a tube shape. The sides are not fused to form a complete tube. The adaxial surface of each of the five lobes is closest to 96C, but does not match any color in the chart. At the base of the lobes is a spot of white not matching any color in the chart, but which appears close to snow white. The spot measures about 2.5 mm. In width. There is a dark bluish spot in the position of about the middle of each lobe of close to 96A to 96B. The base portion from the base of the lobes to the base of the flower is close to 92B with stripes of white not matching any color in the chart, which appear to be snow white. There are tiny spots close to 83B in the top half of the base portion of the petal. The abaxial surface is close to 94D with whitish stripes in the center of the base portion close to, but lighter than, 84D, and not matching any color in the chart but may actually be closer to a milk white.

*Buds.*—Buds prior to opening are 145B to 145C.

*Bud size and shape.*—The buds prior to opening are about 0.5 cm. in length, about 2 to 3 mm. in diameter, and obovate in shape.

*Peduncles.*—There is one flower per peduncle. About 2.5 cm. long and less than 1 mm. in diameter. The color is close to 143A. There is an acicular-shaped leaflet at the point of attachment of the peduncle to the spike, the largest of which is about 3 cm. in length, about 0.4 cm. in width, and is colored close to 147B on the adaxial surface and close to 166A on the abaxial surface.

*Spikes.*—The spike can range in length from 30 cm. to 70 cm. in length, depending on the number of flowers per spike. The internode length is generally between 3 cm. and 5 cm. in length with a width of about 1 mm. The color is 146A.

*Calyx.*—There is one with five lobes. The color is close to 144A, the length is about 2 mm. from the peduncle to the lobes. The lobes are about 0.7 cm. in length, about 1 mm. in width, and the shape is acicular.

*Reproductive organs.*—Ovary is colored close to 144B, about 1 mm. in length, and 1 mm. in diameter. The stigma is about 1 mm. in diameter, and the color is close to 92A with a dark center to close to 93A. The style is about 0.75 cm. in length, about 0.5 mm. in width and with a color close to 145A. The anther is a single organ, which covers the stigma and is shed subsequent to release of the pollen. It has five tiny prongs that extend from the calyx to the tip of the style. The prongs are about 0.75 cm. long and less than 1 mm. wide, and colored close to 92D at the base, and 92A to 92B at the tops. The anter is about 2 mm. long and about 1 mm. wide. The color is close to 93B at the apex, and the base appears close to 202B. The pollen color is closest to 93B. The pollen and anther are shed prior to the stigma being receptive to pollen. As a result, seed production has not been observed without some type of mechanical pollination.

*Disease resistance.*—No susceptibilities were noted, but testing has not been conducted.

*Rooting ability.*—Easy, no hormones needed.

*Fragrance.*—None detected by the inventor.

*Cold/heat resistance.*—The cultivar has flowered continuously in daytime temperatures between 85° F. and 95° F., while the flower of both parents terminated, and the pollen parent expired in the higher temperatures of the range. Plants, if hardened off properly, can tolerate light frosts with little damage.

COMPARISON TO PRIOR ART

The cultivar has only been compared to the parents and the comparison is indicated above.

It is claimed:

1. A new and distinct variety of 'Lobelia erinus' plant, as illustrated and described herein.

* * * * *